United States Patent

Sugiura et al.

(10) Patent No.: US 9,260,458 B2
(45) Date of Patent: Feb. 16, 2016

(54) METHOD OF PRODUCING AN ORGANIC SILICON COMPOUND

(71) Applicant: Dow Corning Toray Co., Ltd., Tokyo (JP)

(72) Inventors: Yasushi Sugiura, Chiba (JP); Yoshinori Taniguchi, Ichihara (JP)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/368,899

(22) PCT Filed: Dec. 25, 2012

(86) PCT No.: PCT/JP2012/084265
§ 371 (c)(1),
(2) Date: Jun. 26, 2014

(87) PCT Pub. No.: WO2013/100166
PCT Pub. Date: Jul. 4, 2013

(65) Prior Publication Data
US 2015/0141689 A1  May 21, 2015

(30) Foreign Application Priority Data

Dec. 27, 2011  (JP) .................................. 2011-285141

(51) Int. Cl.
*C07F 7/16* (2006.01)
*C07F 7/18* (2006.01)
*C07B 49/00* (2006.01)
*C07F 7/08* (2006.01)
*C07F 7/12* (2006.01)

(52) U.S. Cl.
CPC ............... *C07F 7/1876* (2013.01); *C07B 49/00* (2013.01); *C07F 7/0827* (2013.01); *C07F 7/122* (2013.01)

(58) Field of Classification Search
USPC .................................. 556/478, 480, 482, 484
See application file for complete search history.

(56) References Cited

U.S. PATENT DOCUMENTS

| | | | | |
|---|---|---|---|---|
| 2,872,471 | A | * | 2/1959 | Rosenberg et al. ........... 556/480 |
| 7,084,206 | B2 | | 8/2006 | Bedbury et al. |
| 2000/3162985 | | | 8/2003 | Rantala et al. |
| 2003/0233005 | A1 | * | 12/2003 | Nguyen ........................ 556/480 |

FOREIGN PATENT DOCUMENTS

| | | |
|---|---|---|
| JP | 2-53791 | 2/1990 |
| JP | 2002179687 | 6/2002 |
| WO | 2012172177 | 12/2012 |

OTHER PUBLICATIONS

Lee, A.S.Y., et al: "A facile and efficient synthesis of aryltriethoxysilanes via sonochemical Barbier-type reaction", Tetrahedron Letters, Elsevier, Amsterdam, NL, vol. 47, No. 39, Sep. 25, 2006, pp. 7085-7087.
Murata, M. et al.: "Palladium-catalyszed cross-coupling reaction of aryltriethosysilanes with aryl bromides under basic aqueous conditions", Synthesis, Georg Thiem Verlag, Stuttgart, DE, vol. 15, Jan. 1, 2001, pp. 2231-2233.
Benedicte Lebeau et al.: "Synthesis of highly ordered mesoporous hybrid silica from aromatic fluorinated organosilane compound", New J. Chem., vol. 27, 2003, pp. 166-171.
Angiolina Comotti et al.: "2D Multinuclear NMR, hyperpolarized xenon nd gas storage in organosilica nanochannels with crystalline order in the walls", J. Am. Chem. Soc., vol. 129, 2007, pp. 8566-8576.
Oliver Minge et al.:"Triethoxysilane, tetraethoxysilane and hexaethoxysilane—three complementary reagents for the synthesis of hydrogen-rich silylarenes", Z. Naturforsch., vol. 59b, 2004, pp. 153-160.
O'Dell, R.: "A convenient synthesis of arylbis (ethyltrifluorosiliconate)s", Tetrahedron Letters, Elsevier, Amsterdam, NL vol. 36, No. 32, Aug. 7, 1995, pp. 5723-5726.

* cited by examiner

*Primary Examiner* — Sudhakar Katakam
*Assistant Examiner* — Pancham Bakshi
(74) *Attorney, Agent, or Firm* — Matthew T. Fewkes

(57) ABSTRACT

A method of producing an organic silicon compound includes a step of reaction of the following: (A) a reactive silane compound represented by General Formula (1) below: $R^1{}_m SiY_{(4-m)}$ (wherein $R^1$ is a monovalent organic group (except for the group represented by Y) or a hydrogen atom; Y indicates a chlorine atom or a group represented by $-OR^2$; $R^2$ indicates a monovalent hydrocarbon group having 1 to 30 carbon atoms; and m is a number in the range of 0 to 3), (B) a halogenated organic compound represented by General Formula (2) below: $R^3-X$ (wherein $R^3$ indicates a monovalent organic group; and X is a halogen atom), and (C) metallic magnesium (Mg) in the presence of (D) an organic solvent containing at least one type of ether type compound.

3 Claims, No Drawings

METHOD OF PRODUCING AN ORGANIC SILICON COMPOUND

CROSS REFERENCE TO RELATED APPLICATIONS

This application is a U.S. national stage filing under 35 U.S.C. §371 of PCT Application No. PCT/JP12/84265 filed on 25 Dec. 2012, currently pending, which claims the benefit of JP Patent Application No. 2011-285141 filed 27 Dec. 2011 under 35 U.S.C. §119 (a)-(d) and 35 U.S.C. §365(a). PCT Application No. PCT/JP12/84265 and JP Patent Application No. 2011-285141 are hereby incorporated by reference.

FIELD OF THE INVENTION

The present invention relates to a method of producing an organic silicon compound that is capable of shortening the synthesis time in a synthesis process using a Grignard reaction, that is a simple and safe process, that has excellent productivity and reaction selectivity with little generation of waste products, and that has high yield.

BACKGROUND OF THE INVENTION

Organic silicon compounds such as organoalkoxysilanes, organochlorosilanes, or the like having organic groups and alkoxy groups bonded to silicon atoms or having chlorine-bonded silicon atoms are used widely for various types of industrial applications such as electronic materials, construction materials, or the like. A previously known method of producing organic silicon compounds (such as organoalkoxysilanes, organochlorosilanes, or the like) performs synthesis by causing reaction between a reactive organosilane as a raw material (i.e., alkoxysilanes, chlorosilanes, or the like) and a corresponding Grignard reagent in the presence of an ether type solvent such as diethyl ether or tetrahydrofuran. Rather than just diorganodialkoxysilanes, this method is widely used as a method for synthesis of general organoalkoxysilanes. Moreover, a method is known for the production of a phenyl-containing organosilicon intermediate using a phenyl Grignard reagent as a method of producing a phenyl-containing organosilicon intermediate for introduction of an aryl group such as the phenyl group.

For example, although a large amount of ether type solvent (diethyl ether, tetrahydrofuran, or the like) is generally used in order to increase stability of the Grignard reagent, such ether type solvents will readily be oxidized due to atmospheric oxygen to generate peroxides, and the safe handling of such solvents is difficult. Reduction of the utilized amount of ether type solvent is desired even in a large volume industrial production process, and the use of a large amount of ether type solvent has been a problem from the standpoint of safety.

Next, the aforementioned reaction between the Grignard reagent and the reactive silane compound is performed through two reaction steps, i.e. a step (first reaction vessel) for preparation of the Grignard reagent and a step (second reaction vessel) for reaction of the aforementioned Grignard reagent and the organosilane. There have thus been problems in that multiple reaction facilities are required, the time required for synthesis is prolonged, the return rate on reaction (production) facility resources declines, and running costs increase.

Moreover, the conventional generally used production method prepared the Grignard reagent beforehand in the first reaction vessel, transferred the Grignard reagent from the first reaction vessel to the second reaction vessel, and reacted the Grignard reaction with the organosilane. The target organic silicon compound was produced by trickling addition of the organosiloxane to the Grignard reagent to cause reaction between the organosilane and Grignard reagent.

However, when the Grignard reaction is prepared beforehand, the Grignard reagent prepared in the first reaction vessel is unstable. Since the Grignard reagent reacts with moisture and generates heat, the large volume preparation, storage, and liquid transfer of a Grignard reagent have been problematic from the standpoint of safety.

On the other hand, if the reaction is advanced by trickling addition of the organosilane into the Grignard reagent within a solvent such as ether or the like, the reaction occurs by trickling addition of a small amount of organosilane to an excess of Grignard reagent. Thus selectivity of the reaction is lowered, and byproducts thus become readily generated. As a result, the resultant generated product is a mixture of compounds corresponding to values of 0, 1, 2, 3, and 4 for m+n in the compound indicated in the following compounds of General Formula (3). Thus there has been a problem in that the yield of the target organosilane compound decreases.

In addition, after the coupling reaction between the Grignard reagent and the organosilanes, there is a need for removal of the byproduct magnesium salt by centrifugal separation or filtration. However, the salt obtained by separation by filtration includes a large amount of the ether type solvent, and such processing has been accompanied by the danger of exposure of workers to ether type solvent during disposal of the byproduct salt or the like. Although the ether type solvent remaining in the filtrate liquid after filtration may be separated from the target substance by distillation or the like, due to poor stability in the aforementioned manner, this has been accompanied by danger of explosion or fire when the ether based solvent is recycled or discarded. Furthermore, the byproduct salt that is generated when a Grignard reagent is used has high solubility in the ether type solvent. Thus when the ether solvent is removed from the filtrate liquid, there have been problems in that the dissolved byproduct salt precipitates out within the solution of the target substance, separation operations must be performed several times, and productivity and yield of the target organic silicon compound decline.

SUMMARY OF INVENTION

Technical Problem

The object of the present invention is to provide a method of producing an organic silicon compound, particularly an organoalkoxysilane or organochlorosilane, that is capable of shortening the synthesis time in a synthesis process, that is a simple and safe process, that has excellent productivity and reaction selectivity with little generation of waste products, and that has high yield.

Solution to Problems

As a result of dedicated investigations by the inventors of the present invention, the present invention was attained by discovery of the ability to better solve the aforementioned problems by a production method of organic silicon compound represented by General Formula (3)

$$R^1{}_m R^3{}_n SiY_{(4-m-n)}$$

(wherein each $R^1$ is independently a monovalent organic group (except for the group represented by Y) or a hydrogen atom; and each $R^3$ is independently a monovalent organic group; Y is a chlorine atom or a group represented by —OR$^2$; R$^2$ is a monovalent hydrocarbon group having 1 to 30 carbon atoms; and m is a number in the range of 0 to 3; n is a number in the range of 1 to 4; and (m+n) is a number in the range of 1 to 4).

The production method includes a step of reaction of the following: (A) a reactive silane compound represented by General Formula (1) below $R^1{}_mSiY_{(4-m)}$          General Formula(1):

(wherein R$^1$, Y, and m are as defined above for General Formula (3)).

(B) a halogenated organic compound represented by General Formula (2) below $R^3-X$          General Formula (2):

(wherein R$^3$ indicates a monovalent organic group (except for the group represented by Y); and X is a halogen atom), and (C) metallic magnesium (Mg), in the presence of (D) an organic solvent containing at least one type of ether type compound.

Moreover, the inventors of the present invention attained the present invention by discovery of the ability to better solve the aforementioned problems by a method of producing an organic silicon compound that includes a step (I) of mixing the component (A), component (B), and component (D) to obtain a mixed liquid, and a step (II) of causing reaction by trickling addition of the component (B) to the mixed liquid obtained in the step (I).

That is to say, the aforementioned object is attained by the following:

"[1] A method of producing an organic silicon compound represented by General Formula (3)

$R^1{}_mR^3{}_nSiY_{(3-m-n)}$ (wherein R$^1$ to R$^3$ have the same meanings as above; m is the same m as in General Formula (1); n is a number in the range of 1 to 4; and (m+n) is a number in the range of 1 to 4) including a step of reaction of the following:

(A) a reactive silane compound represented by General Formula (1):

$R_mSiY_{(4-m)}$ (wherein R$^1$ is a monovalent organic group (except for the group represented by Y) or a hydrogen atom; Y indicates a chlorine atom or a group represented by —OR$^2$; R$^2$ indicates a monovalent hydrocarbon group having 1 to 30 carbon atoms; and m is a number in the range of 0 to 3)

(B) a halogenated organic compound represented by General Formula (2):

$R^3-X$ (wherein R$^3$ indicates a monovalent organic group (except for the group represented by Y); and X is a halogen atom), (C) metallic magnesium (Mg) in the presence of (D) an organic solvent containing at least one type of ether type compound.

[2] The method of producing an organic silicon compound according to [1];

wherein the method includes: a step (I) of mixing the component (A), component (C), and component (D) to obtain a mixed liquid;

and a step (II) of causing reaction by trickling addition of the component (B) to the mixed liquid obtained in the step (I).

[3] The method of producing an organic silicon compound according to [2];

wherein the steps are performed in the same reaction vessel.

[4] The method of producing an organic silicon compound according to any one of [1] to [3]; wherein the component (A) is a reactive silane compound represented by General Formula (1-1):

$R^1{}_{m1}Si(OR^2)_{(4-m1)}$ (wherein R$^1$ and R$^2$ are groups having the same meaning as above; and m indicates a number in the range of 0 to 3)

and the organic silicon compound is a reactive silane compound represented by General Formula (3-1):

$R^1{}_{m1}R^3{}_{n1}Si(OR^2)_{(4-m1-n1)}$ (wherein R$^1$ to R$^3$ are groups having the same meaning as above; m$^1$ is the same value as m$^1$ of General Formula (1-1); n$^1$ indicates a number in the range of 1 to 4; and (m$^1$+n$^1$) indicates 1 to [5] The method of producing an organic silicon compound according [4]; wherein, in the General Formulae (1-1) and (3-1), R$^1$ is an aryl group, and R$^2$ is a phenyl group or an alkyl group having 1 to 6 carbon atoms;

and in the General Formulae (2) and (3-1), R$^3$ is an aryl group.

[6] The method of producing an organic silicon compound according to any one of [1] to [5]; wherein the utilized amount of the component (D), relative to 1 mol produced amount of the organic silicon compound represented by General Formula (3-1) is in a range of 0.75 to 10.0 mol.

[7] The method of producing an organic silicon compound according to any one of [1] to [6]; wherein the method is for producing an organic silicon compound for use as an optical material.

Advantageous Effects of Invention

According to the present invention, it is possible to provide a method of producing an organic silicon compound that is capable of shortening the synthesis time in a synthesis process, that is a simple and safe process, that has excellent productivity and reaction selectivity with little generation of waste products, and that has high yield.

DETAILED DESCRIPTION OF THE INVENTION

The method of producing an organic silicon compound of the present invention will be described below in detail.

The producing method of the present invention is a method of producing an organic silicon compound represented by General Formula (3) below $R^1{}_mR^3{}_nSiY_{(4-m-n)}$          General Formula(3):

(wherein R$^1$ is a hydrogen atom or a monovalent organic group (except for the group represented by Y); Y is a hydrogen atom or a group represented by OR$^2$; R$^2$ is a monovalent hydrocarbon group having 1 to 30 carbon atoms; R$^3$ is a monovalent organic group (except for the group represented by Y); m is a number in the range of 0 to 3; n is a number in the range of 1 to 4; and (m+n) is a number in the range of 1 to 4).

The method of producing the present invention includes a step of reaction of the following: (A) a reactive silane compound represented by General Formula (1) below $R^1{}_mSiY_{(4-m)}$          General Formula (1):

(wherein R$^1$ is a monovalent organic group (except for the group represented by Y) or a hydrogen atom; Y indicates a chlorine atom or a group represented by —OR$^2$; R$^2$ indicates a monovalent hydrocarbon group having 1 to 30 carbon atoms; and m is a number in the range of 0 to 3

(B) a halogenated organic compound represented by General Formula (2) below $$R^3—X \qquad \text{General Formula (2):}$$

(wherein $R^3$ indicates a monovalent organic group (except for the group represented by Y); and X is a halogen atom), and (C) metallic magnesium (Mg) in the presence of (D) at least one type of ether type compound.

Generally the method that has been adopted for reaction between an organosilane compound and a Grignard reagent uses prior preparation of the Grignard reagent, and then reaction of the Grignard reagent with the organosilane. After preparation of the Grignard reagent, time is required until use for the reaction with the organosilane. The Grignard reagent is diluted in a large excess of ether type solvent so that the Grignard reagent does not become deactivated, and care has been required for storage of the Grignard reagent under an inert gas atmosphere in order to prevent the Grignard reagent from reacting explosively with moisture.

However, due to stabilization of the Grignard reagent by the preparation method of the present invention, there is no need for use of an excess of ether type solvent. That is to say, although the halogenated organic compound (component (B) added by trickling addition reacts with magnesium (component (C) in the reaction vessel to form the Grignard reagent ($R^3$—MgX), the generated Grignard reagent immediately reacts with the reactive silane compound (component (A) present within the reaction vessel to generate the desired organosilane. Thus there is no need for Grignard reagent preparation and storage in the conventional manner, and it is possible to minimize the utilized amount of the ether type solvent. Since there is no need for prior preparation of the Grignard reagent, which reacts violently with water, safe manufacturing is possible in comparison to the conventional method.

By use of this production method, there is no need for production equipment for prior preparation of the Grignard reagent, as had been previously required. It is thus possible to lower running costs and improve return rate on the reaction (production) equipment capital in comparison to the past. In particular, since it becomes possible to obtain the desired compound using only a single reaction vessel, it becomes possible to greatly suppress equipment investment, and the desired compound may be produced with excellent economic efficiency. Moreover, the utilized amount of the ether type solvent may be reduced, and due to the increase in the amount of production per single batch, the desired compound may be produced with good efficiency. The suppression of the utilized amount of ether type solvent is advantageous from the standpoint of safety due to the difficulty of handling the ether type solvent safely due to the ready generation of peroxides due to oxidation by atmospheric oxygen.

Further amazingly, the method of the present invention is able to markedly suppress the side reaction attributable to reaction selectivity in comparison to the production method using the conventional reaction between a Grignard reagent and organosilane, and it is possible to markedly improve yield of the desired compound.

The compound (A) is a reactive silane compound represented by the aforementioned General Formula (1). More specifically, this is one or more types of organosilane represented by General Formula (1), having 0 to 3 organic groups (i.e. $R^1$), selected from among chlorosilanes, organochlorosilanes, organoalkoxysilanes, organoalkoxychlorosilanes, and alkoxysilanes. In the present invention, Component (A) is preferably a tetraalkoxysilane, organotrialkoxysilane, diorganodialkoxysilane, triorganoalkoxysilane, tetrachlorosilane, organotrichlorosilane, diorganodichlorosilane, or triorganochlorosilane.

In General Formula (1), $R^1$ is a monovalent organic group (except for the group represented by Y) or a hydrogen atom, and is the same functional group as $R^1$ in the organic silicon compound represented by General Formula (3) after the Grignard reaction. No particular limitation is placed on the utilized $R^1$, whether a reactive or non-reactive functional group, as long as $R^1$ isn't a chlorine atom and isn't the alkoxy functional group (—Y) represented by —$OR^2$. $R^1$ is preferably an organic group having 1 to 30 carbon atoms. Particularly preferred examples include alkyl groups, alkenyl groups, alkynyl groups, aryl groups, halogenated alkyl groups, halogenated aryl groups, acryloxy groups, or the like. Furthermore, the carbon atoms in such functional groups may be optionally substituted by a nitrogen atom (amino group), oxygen atom, silicon atom, sulfur atom, phosphorous atom, or the like.

Particularly when the method of the present invention of producing an organic silicon compound is used to produce an optical material capable of industrial use, $R^1$ is preferably a linear or branched alkyl group, cycloalkyl group, alkenyl group, aryl group, or acryloxy group. $R^1$ is particularly preferably a monovalent organic group selected as at least one type from among the methyl group, ethyl group, propyl group, hexyl group, vinyl group, propenyl group, hexenyl group, cyclohexyl group, acryloxy group, methacryloxy group, phenyl group, and naphthyl group.

In General Formula (1), Y is a chlorine atom or a group represented by —$OR^2$. $R^2$ is a monovalent hydrocarbon group having 1 to 30 carbon atoms. The group represented by —$OR^2$ forms an alkoxy group. Thus $R^2$ is preferably an alkyl group or an aryl group having 1 to 30 carbon atoms. From the standpoint of industrial usability and the use of the method of the present invention for production of an organosilane as an optical raw material, $R^2$ is preferably a linear or branched alkyl group or a phenyl group having 1 to 6 carbon atoms. In this case, the group represented by —$OR^2$ is exemplified by the methoxy group, ethoxy group, propoxy group, isopropoxy group, butoxy group, phenoxy group, or the like. In the present invention, Y is preferably a chlorine atom, methoxy group, ethoxy group, or phenoxy group. Y is particularly preferably an alkoxy group such as the methoxy group, ethoxy group, or phenoxy group.

In General Formula (1), m is a number in the range of 0 to 3. When m is equal to 0, the component (A) is tetrachlorosilane or a tetraalkoxysilane. When m is equal to 3, the component (A) is a (tri)organochlorosilane or a (tri)organoalkoxysilane. Preferably m is a number in the range of 0 to 2. If Y is an alkoxy group, component (A) is preferably a diorganodialkoxysilane, organotrialkoxysilane, or tetraalkoxysilane.

Specifically, the component (A) is exemplified by the below listed chlorosilanes and alkoxysilanes, without particular limitation. As may be required, a mixture of two or more types of organosilanes may be used as the component (A) organosilane.

The component (A) is exemplified by: methyltrimethoxysilane, dimethyldimethoxysilane, trimethylmethoxysilane, methyltriethoxysilane, dimethyldiethoxysilane, trimethylethoxysilane, vinyltrimethoxysilane, vinylmethyldimethoxysilane, vinyldimethylmethoxysilane, vinyltriethoxysilane, vinylmethyldiethoxysilane, vinyldimethylethoxysilane, phenyltrimethoxysilane, diphenyldimethoxysilane, triphenylmethoxysilane, phenylmethyldimethoxysilane, diphenylmethylmethoxysilane, phenyldimethylmethoxysilane, phenylvinyldimethoxysilane, phenyldivinylmethoxysilane, diphenylvinylmethoxysilane, phenyltriethoxysilane, diphenyldiethoxysilane, triphenylethoxysilane, phenylmethyldiethoxysilane, diphenylmethylethoxysilane, phenyldimethylethoxysilane, phenylvinyldiethoxysilane, phenyldivinylethoxysilane, diphenylvinylethoxysilane, cyclohexyltrimethoxysilane, dicyclohexyldimethoxysilane, cyclohexyltriethoxysilane, dicyclohexyldiethoxysilane, cyclohexylmethyldimethoxysilane, dicyclohexylmethylmethoxysilane, cyclohexyldimethylmethoxysilane, cyclohexylvinyltrimethoxysilane, dicyclohexylvinylmethoxysilane, cyclohexyldivinyltrimethoxysilane, cyclohexylphenyldimethoxysilane, dicyclohexylphenylmethoxysilane, cyclohexyldiphenylmethoxysilane, tolyltrimethoxysilane, phenyltolyldimethoxysilane, tolylmethyldimethoxysilane, tetramethoxysilane, tetraethoxysilane, tetrachlorosilane, methyltrichlorosilane, 1-naphthyltrimethoxysilane, 2-naphthyltrimethoxysilane, di(1-naphthyl)dimethoxysilane, 1-naphthyl-2-naphthyldimethoxysilane, 1-naphthylmethyldimethoxysilane, 2-naphthylmethyldimethoxysilane, 1-naphthylphenyldimethoxysilane, 2-naphthylphenyldimethoxysilanemethyltrichlorosilane, dimethyldichlorosilane, trimethylchlorosilane, vinyltrichlorosilane, divinyldichlorosilane, vinylmethyldichlorosilane, ethyltrichlorosilane, diethyldichlorosilane, ethylmethyldichlorosilane, 3-propyltrichlorosilane, 3-propylmethyldichlorosilane, 3-pentyltrichlorosilane, 3-pentylmethyldichlorosilane, cyclopentyltrichlorosilane, cyclopentylmethyldichlorosilane; 6-hexyltrichlorosilane, 6-hexylmethyldichlorosilane, cyclohexyltrichlorosilane, cyclohexylmethyldichlorosilane, phenyltrichlorosilane, diphenyldichlorosilane, triphenylchlorosilane, 1-naphthyltrichlorosilane, di(1-naphthyl)dichlorosilane, 1-naphthylmethyldichlorosilane, 1-naphthylphenyldichlorosilane, 2-naphthyltrichlorosilane, di(2-naphthyl)dichlorosilane, 1-naphthyl-2-naphthyldichlorosilane, 2-naphthylmethyldichlorosilane, and 2-naphthylphenyldichlorosilane.

The component (B) is a halogenated organic compound represented by the aforementioned General Formula (2). Within this formula, $R^3$ is a monovalent organic group introduced to the target organoalkoxysilane (represented by General Formula (3)) by the Grignard reaction. $R^3$ is a reactive or non-reactive functional group, and is a functional group other than the chlorine atom or the alkoxy group represented by $-OR^2$. Any such group may be used without particular limitation as $R^3$ as long as use of the Grignard reaction is possible. Such monovalent organic groups are exemplified by the same groups as for $R^1$ above. However, from the standpoints of industrial usability and use of the method of the present invention for production of an organoalkoxysilane as an optical raw material, $R^3$ is preferably a linear or branched alkyl group, cycloalkyl group, alkenyl group, or aryl group. $R^3$ is particularly preferably one or more type of monovalent organic group selected from among the methyl group, ethyl group, propyl group, hexyl group, vinyl group, propenyl group, hexenyl group, cyclohexyl group, acryloxy group, methacryloxy group, phenyl group, tolyl group, and naphthyl group. Particularly an alkenyl group (such as the vinyl group, propenyl group, or the like) or an aryl group (such as the phenyl group, naphthyl group, or the like) may be used as $R^3$ from the standpoint of excellent selectivity of the obtained organic silicon compound in comparison to selectivity of the normal Grignard reaction and due to the ability to remarkably reduce the amount of organic solvent used in the reaction.

wherein X is a halogen atom, and this halogen atom is preferably bromine or chlorine. From the standpoint of industrial usability and use in a method of the present invention for production of an optical raw material, the component (B) is exemplified by one or more types of halogenated organic compounds, without particular limitation. As may be required, the component (B) may be used as a mixture of two or more types.

Component (B) is exemplified by: methyl chloride, ethyl chloride, propyl chloride, isopropyl chloride, n-butyl chloride, sec-butyl chloride, tert-butyl chloride, vinyl chloride, 2-propenyl chloride, 3-butenyl chloride, phenyl chloride, o-dichlorobenzene, m-dichlorobenzene, p-dichlorobenzene, 1,3,5-trichlorobenzene, o-tolyl chloride, m-tolyl chloride, p-tolyl chloride, 1-methyl-3,5-dichlorobenzene, 1-naphthyl chloride, 2-naphthyl chloride, methyl bromide, ethyl bromide, propyl bromide, isopropyl bromide, n-butyl bromide, sec-butyl bromide, tert-butyl bromide, vinyl bromide, 2-propenyl bromide, 3-butenyl bromide, phenyl bromide, o-tolyl bromide, m-tolyl bromide, p-tolyl bromide, 1-naphthyl bromide, 2-naphthyl bromide, o-dibromobenzene, m-dibromobenzene, p-dibromobenzene, 1,3,5-tribromobenzene, and 1-methyl-3,5-dibromobenzene.

The component (C) is magnesium, and this component reacts with the halogenated organic compound component (B) supplied into the system and generates the Grignard reagent ($R^3MgX$). Any metallic magnesium may be used as the metallic magnesium utilized in the reaction of the present invention. Chip-like, powder-like, flake-like, spheroid-like, etc. Magnesium powder is particularly preferably used. Moreover, the magnesium may be used as an alloy with another type of metal as long as the technical effect of the present invention is not inhibited.

The component (D) is an organic solvent including at least one type of ether type organic solvent. The organic solvent is exemplified by ether type solvents such as diethyl ether, tetrahydrofuran, tert-butyl methyl ether, 1,4-dioxane, 1,2-dimethoxyethane, or the like. Any amount of the ether type solvent may be used. However, if the utilized amount of ether type solvent is excessively low, the reaction between the metallic magnesium and the halogenated organic component becomes remarkably prolonged. The reaction time preferably is not prolonged. On the other hand, use of an excessive amount of ether type solvent is undesirable due to problems such as cost increase due to excessive use of solvent, decline of productivity due to lowering of the reaction concentrations, difficulty of removal of reaction byproduct magnesium salts due to dissolution, or the like. Therefore the utilized amount of the ether type solvent is preferably in the range of 0.75 to 5.0 mol per 1 mol of the generated amount of the organic silicon compound represented by General Formula (3), and this utilized amount is particularly preferably in the range of 0.75 to 2.0 mol. Any hydrocarbon type inert organic solvent, as exemplified by hexane, toluene, xylene, or the like, may be added to the ether type organic solvent.

As described above, by execution of the production method of the present invention particularly using the component (B) having an aryl group, in comparison to the normal Grignard reaction, the utilized amount of such ether type solvents is suppressed, and it is possible to realize high reaction selectivity. Moreover, the suppression of the utilized amount of the ether type solvent has the advantages of compatibility with the environment and the ability to perform the reaction safely and at low cost.

Temperature of the reaction is preferably in the range of 0 to 200° C., and particularly preferably is in the range of 20 to 150° C. Moreover, when oxygen is present in the reaction system, reaction intermediates are generated from oxidation of the Grignard reagent generated within the reaction apparatus then react with the component (A), byproducts having boiling points near that of the target compound are generated, and purification by distillation becomes difficult. Moreover, peroxides are generated by oxidation of the ether type compound used as the solvent, and thus this reaction is preferably performed under an inert gas atmosphere, i.e. nitrogen, argon, or the like. Moreover, if water is present in the reaction system, when the organic halogenated compound is added dropwise, and the water reacts with the generated Grignard reagent so that the yield and purity of the target compound decline. Utilized raw materials preferably have had moisture removed as much as possible.

Although the time required for reaction may be any amount of time, if the reaction is not completed after trickling addition of the halogenated organic compound (B), stirring may be continued to allow completion of the reaction. Although any reaction temperature may be used during this completion of the reaction, temperature is preferably in the range of 0 to 200° C., and particularly preferably is in the range of 20 to 150° C.

After completion of the reaction, the byproduct salt may be removed by filtration, centrifugal separation, or water washing. When the slurry fed to centrifugal separation includes an ether type solvent, the byproduct salt dissolves in the ether type solvent, and magnesium salt precipitates out during the following process. Thus prior to filtration or centrifugal separation, the ether type solvent is preferably removed by distillation or the like. On the other hand, in a process that removes (distills off) the ether type solvent after performance of filtration or centrifugal separation, salts sometimes reprecipitate after the solvent distillation, and supplemental filtration or centrifugal separation to separate out the byproduct salt is preferably used.

After separation from the byproduct salt, the target organic silicon compound is included in the organic solvent. Thus the organic silicon compound may be isolated and purified by a suitable normal method such as distillation or the like.

According to the production method of the present invention, by suitable selection of the types of the component (A) and component (B), it is possible to produce the aforementioned organic silicon compound represented by General Formula (3) without particular limitation. No particular limitation is placed on this production process as long as the process includes causing reaction of the component (A) and component (B) in the presence of the component (C) and component (D). The process may be performed in the same reaction apparatus or may be accompanied by transfer of the reaction raw materials to two or more reaction apparatuses. However, from the standpoint of production process simplification and industrial productivity, after step (I) of mixing said components (A), (C), and (D) in the same reaction apparatus (reaction vessel), the aforementioned component (B) is particularly preferably added dropwise to the mixed solution obtained during step (I) to perform the reaction of step (II).

By selection of this production process, it is possible to reduce the synthesis time in a synthesis process using the Grignard reaction, it is possible to simply and safely feed the raw material, it is possible to perform the reaction with good efficiency, it is possible to suppress the amount of formed waste products, and it is possible to improve productivity, reaction selectivity, and reaction yield.

No particular limitation is placed on the organic silicon compound obtained by the production method of the present invention as long as this compound is represented by the General Formula (3), and the below listed organosilanes, organoalkoxysilanes, and organochlorosilanes may be obtained with good yield. The production method of the present invention is particularly suitable for production of an organic silicon compound having an alkyl group, aryl group, or alkoxy group or having a chlorine atom directly bonded to silicon. The production method of the present invention is suitable for synthesis of tetraarylsilanes, triarylalkoxysilanes, diaryldialkoxysilanes, and triarylalkoxysilanes. The production method of the present invention is particularly suitable for synthesis of diphenyldimethoxysilane, diphenyldiethoxysilane, phenyltrimethoxysilane, phenyltriethoxysilane, dinaphthyldimethoxysilane, dinaphthyldiethoxysilane, naphthyltrimethoxysilane, naphthyltriethoxysilane, phenyltrichlorosilane, diphenyldichlorosilane, 1-naphthyltrichlorosilane, 2-naphthyltrichlorosilane, and di(1-naphthyl)dichlorosilane.

Additionally, the organic silicon compound obtained by the present invention is exemplified by the following:
vinyltrichlorosilane, vinylmethyldichlorosilane, vinyldimethylchlorosilane, vinyltrimethoxysilane, vinylmethyldimethoxysilane, vinyldimethylmethoxysilane, vinyltrimethylsilane, vinyltriethoxysilane, vinylmethyldiethoxysilane, vinyldimethylethoxysilane, divinyldimethylsilane, trivinylmethylsilane, tetravinylsilane, allyltrichlorosilane, allylmethyldichlorosilane, allyldimethylchlorosilane, allyltrimethylsilane, allyltrimethoxysilane, allylmethyldimethoxysilane, allyldimethylmethoxysilane, allyltriethoxysilane, allylmethyldiethoxysilane, allyldimethylethoxysilane, diallyldimethylsilane, diallyldimethoxysilane, triallylmethylsilane, triallylmethoxysilane, tetraallylsilane, cyclohexyltrichlorosilane, cyclohexylmethyldichlorosilane, cyclohexyldimethyichlorosilane, cyclohexyltrimethoxysilane, cyclohexylmethyldimethoxysilane, cyclohexyldimethylmethoxysilane, cyclohexyltriethoxysilane, cyclohexylmethyldiethoxysilane, cyclohexyldimethylethoxysilane, phenyltrimethoxysilane, diphenyldimethoxysilane, phenylmethyldimethoxysilane, triphenylmethoxysilane, diphenylmethylmethoxysilane, tetraphenylsilane, triphenylmethylsilane, diphenyldimethylsilane, [misspelling of "phenyltrichlorosilane"], diphenyldichlorosilane, phenylmethyldichlorosilane, triphenylchlorosilane, phenylvinyldichlorosilane, divinylphenylchlorosilane, diphenyldivinylchlorosilane, phenylvinyldimethoxysilane, divinylphenylmethoxysilane, diphenyldivinylmethoxysilane, phenyltriethoxysilane, diphenyldiethoxysilane, phenylmethyldiethoxysilane, triphenylethoxysilane, diphenylmethylethoxysilane, tetraphenylsilane, diphenylmethylchlorosilane, 1,2-di(trimethoxysilyl)benzene, 1,3-di(trimethoxysilyl)benzene, 1,4-di(trimethoxysilyl)benzene, 1,2-di(trichlorosilyl)benzene, 1,3-di(trichlorosilyl)benzene, 1,4-di(trichlorosilyl)benzene, 1,2-di(methyldimethoxysilyl)benzene, 1,3-di(methyldimethoxysilyl)benzene, 1,4-di(methyldimethoxysilyl)benzene, 1,2-di(methyldichlorosilyl)benzene, 1,3-di(methyldichlorosilyl)benzene, 1,4-di(methyldichlorosilyl)benzene, 1,2-di(dimethylchlorosilyl)benzene, 1,3-di(dimethylchlorosilyl)benzene, 1,4-di(dimethylchlorosilyl)benzene, 1,2-di(dimethylmethoxysilyl)benzene, 1,3-di(dimethylmethoxysilyl)benzene, 1,4-di(dimethylmethoxysilyl)benzene, 1,3,5-tris(trimethoxysilyl)benzene, 1,3,5-tris(trichlorosilyl)benzene, 1,3,5-tris(methyldichlorosilyl)benzene, 1,3,5-tris(methyldimethoxysilyl)benzene, 1,3,5-tris(dimethylchlorosilyl)benzene, 1,3,5-tris(dimethylmethoxysilyl)benzene, 1-naphthyltrimethoxysilane, 1-naphthyltriethoxysilane, di(1-naphthyl)dimethoxysilane, tri(1-naphthyl)methoxysilane, tetra(1-naphthyl)silane, 1-naphthylmethyldimethoxysilane, 1-naphthyldimethylmethoxysilane, 1-naphthylphenyldimethoxysilane, 1-naphthyldiphenylmethoxysilane, 2-naphthyltrimethoxysilane, 2-naphthyltriethoxysilane, di(2-naphthyl)dimethoxysilane, tri(2-naphthyl)methoxysilane, tetra(2-naphthyl)silane, 2-naphthylmethyldimethoxysilane, 2-naphthyldimethylmethoxysilane, 2-naphthylphenyldimethoxysilane, 2-naphthyldiphenylmethoxysilane, 1-naphthyl-2-naphthyldimethoxysilane, di(1-naphthyl)-2-naphthylmethoxysilane, and 1-naphthyl-di(2-naphthyl)methoxysilane.

EXAMPLES

Hereinafter, the present invention is described in detail with reference to Practical Examples and Comparative Examples, but it should be understood that the present invention is not limited to these Practical Examples. Purity measurement and identification of the organic compounds were performed by the below described methods.

[Method of Measurement of Organic Silicon Compound Purity (%)]

Gas chromatograph (manufactured by Shimadzu Corp.), model no. GC-2010, DB-5 J&W column manufactured by Agilent Technologies, Inc., carrier gas: helium, carrier gas flow rate: 50 mL/minute, 80° C. injection port temperature, detector (TCD) temperature: 280° C., heat-up rate of 15° C./minute.

[Method of Identification of the Organic Silicon Compound]

Gas chromatograph-mass spectrometer (GC-MS, manufactured by Shimadzu Corp.), model no. QP-5050, DB-5 GC column manufactured by Agilent Technologies, Inc., carrier gas: helium, carrier gas flow rate: 20 mL/minute, 80° C. injection port temperature, detector temperature: 280° C., heat-up rate of 15° C./minute.

Synthesis of Diphenyldimethoxysilane

Comparative Example 1, Practical Examples 1 to 3

Results of performing synthesis of diphenyldimethoxysilane by the normal method and by the method of the present application invention are represented in Comparative Example 1 (normal method) and Practical Examples 1 to 3. With the object of performing a comparison of reaction selectivity, Practical Example 3 was an experiment using the same amount of ether type solvent as that of Comparative Example 1.

The synthesized compound contents and byproducts of the comparative example and practical examples are listed in Table 1.

Comparative Example 1

500 mL of a phenyl magnesium chloride solution (produced by Sigma-Aldrich, 32 percent by weight tetrahydrofuran solution, 2 mol/L, 1.0 mol equivalents of phenyl magnesium chloride) was loaded into a 1 L 4-neck flask equipped with a nitrogen gas feed tube, thermometer, Dimroth type condenser, and dripping funnel. While the mixture was stirred, the mixture was heated to 60° C. Thereafter, 193.8 g (1.0 mol) of phenyltrimethoxysilane was added dropwise at 60 to 70° C. After completion of trickling addition, the mixture was further stirred for 1 h at 70° C., and then was cooled to 30° C. The generated slurry was suction filtered using glass filter paper GC90 manufactured by Advantec, and the byproduct methoxymagnesium bromide was removed by filtration. The tetrahydrofuran was removed by distillation using an evaporator to obtain 200.2 g of the product. The product was confirmed by MS-GC to be diphenyldimethoxysilane(66.1% purity).

Practical Example 1

24.3 g (1.0 mol) of flake-like magnesium produced by Wako Pure Chemical Industries, Ltd. (1.74 specific gravity), 54.0 g (0.75 mol) of tetrahydrofuran produced by Tokyo Chemical Industry Co., Ltd., 92.1 g (1.0 mol) of toluene produced by Tokyo Chemical Industry Co., Ltd., and 198.3 g (1.0 mol) of phenyltrimethoxysilane (Z-6126 SILANE) produced by Dow Corning were loaded into a 1 L 4-neck flask equipped with a nitrogen gas feed tube, thermometer, Dimroth type condenser, and dripping funnel. While the mixture was stirred, the mixture was heated to 60° C. Thereafter, 157.0 g (1.0 mol) of phenyl bromide produced by Sigma-Aldrich was added dropwise at 60 to 70° C. After completion of trickling addition, the mixture was further stirred for 1 h, and then was cooled to 30° C. The generated slurry was suction filtered using glass filter paper GC90 manufactured by Advantec, and the byproduct methoxymagnesium bromide was removed by filtration. The tetrahydrofuran was removed by distillation using an evaporator to obtain 232.0 g of the product. The product was confirmed by GC-MS to be diphenyldimethoxysilane (86.8% purity).

Practical Example 2

Synthesis was performed by the same method as that of Practical Example 1 except for changing the utilized amount of tetrahydrofuran to 180.3 g (2.5 mol).

Practical Example 3

Synthesis was performed by the same method as that of Practical Example 1 except for changing the utilized amount of tetrahydrofuran to 385.3 g (5.3 mol).

TABLE 1

|  | Comparative Example 1 | Practical Example 1 | Practical Example 2 | Practical Example 3 |
|---|---|---|---|---|
| phenyltrimethoxysilane content (%)[1] | 14.3 | 6.7 | 6.5 | 6.9 |
| diphenyldimethoxysilane content (%)[1] | 66.1 | 86.8 | 87.3 | 86.5 |
| triphenylmethoxysilane content (%)[1] | 14.4 | 6.3 | 5.9 | 6.3 |
| tetraphenylsilane (%) content[1] | 5.2 | 0.2 | 0.3 | 0.3 |
| utilized tetrahydrofuran amount[2] or [3] | 5.3[3] | 0.75[2] | 2.5[2] | 5.3[2] |
| cycle time (h) | 15 | 9 | 8.5 | 9 |

[1] results of gas chromatography analysis
[2] utilized amount of tetrahydrofuran (mol) per 1 mol of phenyl bromide
[3] utilized amount of tetrahydrofuran (mol) per 1 mol of phenyl magnesium bromide Synthesis of 1-Naphthyltrimethoxysilane Comparative Example 2, Practical Examples 4 to 6

Results of performing synthesis of 1-naphthyltrimethoxysilane by the normal method and by the method of the present application invention are represented in Comparative Example 2 (normal method) and Practical Examples 4 to 6. The normal method required use of 47.3 equivalents (mol) of tetrahydrofuran relative to the 1-naphthyl magnesium bromide. The synthesized compound contents and byproducts of the comparative example and practical examples are listed in Table 2.

Comparative Example 2

Preparation of the Grignard Reagent 24.3 g (1.0 mol) of flake-like magnesium produced by Wako Pure Chemical Industries, Ltd. (1.74 specific gravity) and 3,410.3 g (47.3 mol) of tetrahydrofuran produced by Tokyo Chemical Industry Co., Ltd. were loaded into a 5 L 4-neck flask equipped with a nitrogen gas feed tube, thermometer, Dimroth type condenser, and dripping funnel. While the mixture was stirred, the mixture was heated to 40° C. Thereafter, 207.1 g (1.0 mol) of 1-bromonaphthalene was added dropwise at 30 to 40° C. After the mixture was stirred further for 2 h at 40° C., the mixture was cooled to 30° C. to obtain a 1-naphthyl magnesium bromide tetrahydrofuran solution (0.25M) as a slurry.

Synthesis of 1-Naphthyltrimethoxysilane 609.2 g (4.0 mol) of tetramethoxysilane produced by Tama Chemicals Co., Ltd. was loaded into a 10 L 4-neck flask equipped with a nitrogen gas feed tube, thermometer, Dimroth type condenser, and dripping funnel. While the mixture was stirred, the mixture was heated to 60° C. Thereafter, the previously prepared 1-naphthyl magnesium bromide tetrahydrofuran solution (3,641.4 g, 1.0 mol equivalent of 1-naphthyl magnesium bromide) was added dropwise at 20 to 30° C. After completion of trickling addition, the mixture was stirred for a further 1 h at 70° C., and then the mixture was cooled to 30° C. The generated slurry was suction filtered using glass filter paper GC90 manufactured by Advantec, and the byproduct methoxymagnesium bromide was removed by filtration. The tetrahydrofuran and unreacted tetramethoxysilane were removed by distillation using an evaporator to obtain 221.4 g of the product. The product was confirmed by GC-MS to be 1-naphthyltrimethoxysilane (61.1% purity).

Practical Example 4

26.95 g (1.0 mol) of flake-like magnesium produced by Wako Pure Chemical Industries, Ltd. (1.74 specific gravity), 108.15 g (1.5 mol) of tetrahydrofuran produced by Tokyo Chemical Industry Co., Ltd., 92.1 g (1.0 mol) of toluene produced by Tokyo Chemical Industry Co., Ltd., and 609.2 g (4.0 mol) of tetramethoxysilane produced by Tama Chemicals Co., Ltd. were loaded into a 1 L 4-neck flask equipped with a nitrogen gas feed tube, thermometer, Dimroth type condenser, and dripping funnel. While the mixture was stirred, the mixture was heated to 30° C. Thereafter, 207.1 g (1.0 mol) of 1-bromonaphthalene was added dropwise at 20 to 30° C. After completion of trickling addition, the mixture was further stirred for 1 h at 70° C., and then was cooled to 30° C. The generated slurry was suction filtered using glass filter paper GC90 manufactured by Advantec, and the byproduct methoxymagnesium bromide was removed by filtration. The tetrahydrofuran and the unreacted tetramethoxysilane were removed by distillation using an evaporator to obtain 232.0 g of the product. The product was confirmed by GC-MS to be 1-naphthyltrimethoxysilane (89.9% purity).

Practical Example 5

Synthesis was performed by the same method as that of Practical Example 4 except for changing the utilized amount of tetrahydrofuran to 180.3 g (2.5 mol).

Practical Example 6

Synthesis was performed by the same method as that of Practical Example 4 except for changing the utilized amount of tetrahydrofuran to 288.4 g (4.0 mol).

TABLE 2

|  | Comparative Example 2 | Practical Example 4 | Practical Example 5 | Practical Example 6 |
|---|---|---|---|---|
| 1-naphthyltrimethoxysilane content (%)[1] | 61.1 | 89.9 | 90.1 | 89.0 |
| di(1-naphthyl)dimethoxysilane content (%)[1] | 31.1 | 7.2 | 6.8 | 6.2 |
| tri(1-naphthyl)methoxysilane content (%)[1] | 7.8 | 3.9 | 3.1 | 4.8 |
| utilized tetrahydrofuran amount[2] or [3] | 47.3[3] | 1.5[2] | 2.5[2] | 4.0[2] |
| cycle time (h) | 21 | 11 | 12 | 13 |

[1]results of gas chromatography analysis
[2]utilized amount of tetrahydrofuran (mol) per 1 mol of 1-naphthyltrimethoxysilane
[3]utilized amount of tetrahydrofuran (mol) per 1 mol of 1-naphthyl magnesium bromide As indicated by Comparative Example 1 and Practical Examples 1 to 3, the production method of the present application invention has more excellent selectivity than the normal method, is able to synthesize phenyltrimethoxysilane, and is able to promote reaction without difficulty even though the utilized amount of ether type solvent was lower than that of the normal method. Furthermore, as indicated by Comparative Example 2 and Practical Examples 4 to 6, the production method of the present application invention has more excellent selectivity than the normal method, is able to synthesize naphthyltrimethoxysilane, and is able to markedly suppress the utilized amount of ether type solvent in comparison to the normal method.

INDUSTRIAL APPLICABILITY

Among the organic silicon compounds obtained by the production method of the present invention, aryl group-containing organic silicon compounds having the phenyl group or naphthyl group form high refractive index polymers by hydrolysis/condensation polymerization reaction. It is thus possible to use such polymers with advantage as optical raw materials requiring high refractive index and transparency. By use of the production method of the present invention, it is possible to produce organic silicon compounds safely and with good efficiency, and it is possible to control production costs. Therefore high value-added optical raw material of high purity may be provided inexpensively and in large amounts.

The invention claimed is:
1. A method of producing an organic silicon compound of General Formula (3):

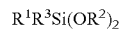

$R^1R^3Si(OR^2)_2$ (wherein $R^1$ is an aryl group; $R^3$ is an aryl group; $R^2$ indicates an alkyl group having 1 to 6 carbon atoms,
wherein the method comprises reacting the following:
(A) a reactive silane compound of formula (1):

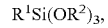

$R^1Si(OR^2)_3$, where R1 and R2 are as defined above,
(B) a halogenated organic compound of formula (2):

$R^3—X$ (wherein $R^3$ is as defined above; and X is a halogen atom), and (C) metallic magnesium (Mg) in the presence of (D) an organic solvent containing ether functionality, and wherein the method comprises a Step (I) of mixing said (A), (C), and (D) to obtain a mixed liquid;

and a step (II) of causing reaction by addition of said (B) to said mixed liquid obtained in said step (I).

2. The method of producing an organic silicon compound according to claim 1; wherein said steps are performed in the same reaction vessel.

3. The method of producing an organic silicon compound according to claim 1; wherein the amount of component (D), relative to 1 mol produced amount of the organic silicon compound represented by General Formula (3), is in a range of 0.75 to 10.0 mol.

\* \* \* \* \*